United States Patent [19]

Stenberg et al.

[11] 4,239,728
[45] Dec. 16, 1980

[54] APPARATUS AND METHOD FOR THE DIFFUSION OF SUBSTANCES BETWEEN TWO FLUIDS SEPARATED BY A SEMIPERMEABLE MEMBRANE

[75] Inventors: Kaj O. Stenberg, Staffanstorp; Lars J. C. Travén, Lund, both of Sweden

[73] Assignee: Gambro AB, Sweden

[21] Appl. No.: 6,248

[22] Filed: Jan. 24, 1979

[30] Foreign Application Priority Data

Feb. 2, 1978 [SE] Sweden ............................ 7801231

[51] Int. Cl.³ ............................................ A61M 1/03
[52] U.S. Cl. ................................. 422/46; 128/DIG. 3; 55/158; 261/DIG. 28; 422/47; 422/48
[58] Field of Search .................. 422/45, 46, 47, 48; 210/23 R, 150, 175, 180, 181, 188, 307, 321 B, 335; 128/DIG. 3; 55/16, 158; 261/DIG. 28

[56] References Cited

U.S. PATENT DOCUMENTS

| | | | |
|---|---|---|---|
| 3,034,505 | 5/1962 | Sobol | 210/321 B |
| 3,332,746 | 7/1967 | Claff et al. | 422/48 |
| 3,398,091 | 8/1968 | Greatorex | 210/321 R |
| 3,413,095 | 11/1968 | Bramson | 210/321 B |
| 3,488,158 | 1/1970 | Bentley et al. | 422/47 |
| 3,594,130 | 3/1969 | North, Jr. | 422/48 |
| 3,651,616 | 3/1972 | Blanchard et al. | 55/16 |
| 3,684,097 | 8/1972 | Mathewson, Jr. et al. | 210/321 |
| 3,768,653 | 10/1973 | Brumfield | 210/188 |

OTHER PUBLICATIONS

"Heart Surgery with a Membrane Oxygenator in Infants" Journ. of Thor. and Card. Surgery, Sugg et al, vol. 67 #4 Apr. 1974.
"Heart-Lung Bypass" P.M. Galletti et al. Grune and Stratten, NY 1962, pp. 156-159.
"Clinical Evaluation of Harvey H200 Oxygenator" Page et al., Jour. Of Thor. and Card. Surgery, vol. 67 #2, Feb. 1974.
"The Infant Temptrol Oxygenator" Clark et al., Journ. of Thor. and Card. Surgery, vol. 60 #1, Jul. 1970.

*Primary Examiner*—Charles N. Hart
*Assistant Examiner*—David R. Sadowski
*Attorney, Agent, or Firm*—Lerner, David, Littenberg & Samuel

[57] ABSTRACT

An apparatus and method for the diffusion of substances between two fluids. The apparatus comprises at least one semipermeable membrane having first and second opposing surfaces, first conducting means for conducting a first fluid along the first surface of the membrane, and second conducting means for conducting a second fluid along a second surface of the membrane. The membrane is permeable to a portion of the first fluid so that at least a part of the portion of the first fluid is diffused through the membrane into the second fluid during conduction of the first and second fluids along the opposing surfaces of the membrane. Mixing means are provided for directly mixing the first fluid into the second fluid after conduction of the first fluid along the first surface of the membrane. In the preferred embodiment, this mixing means comprises apertures at the downstream end of the membrane for introducing the first fluid directly into the second fluid flowing on the opposite side of the membrane.

21 Claims, 21 Drawing Figures

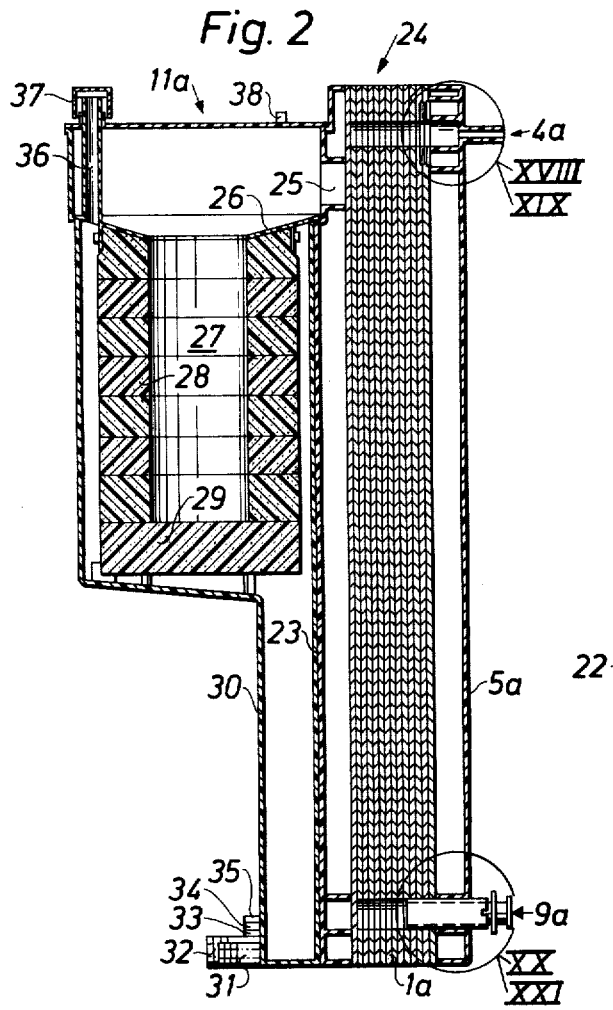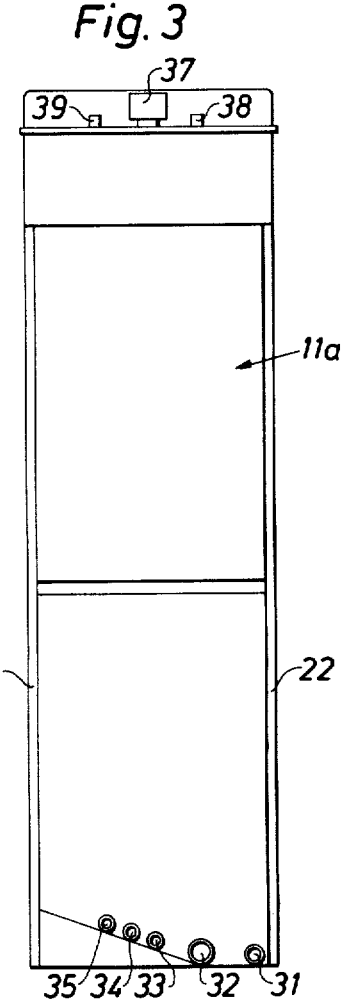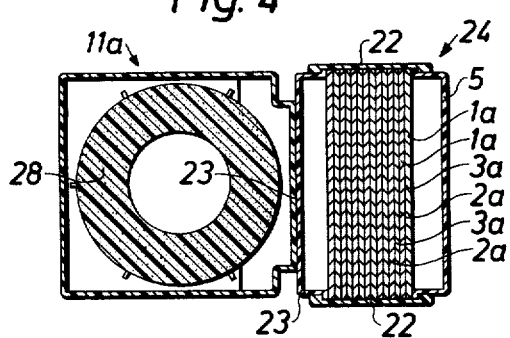

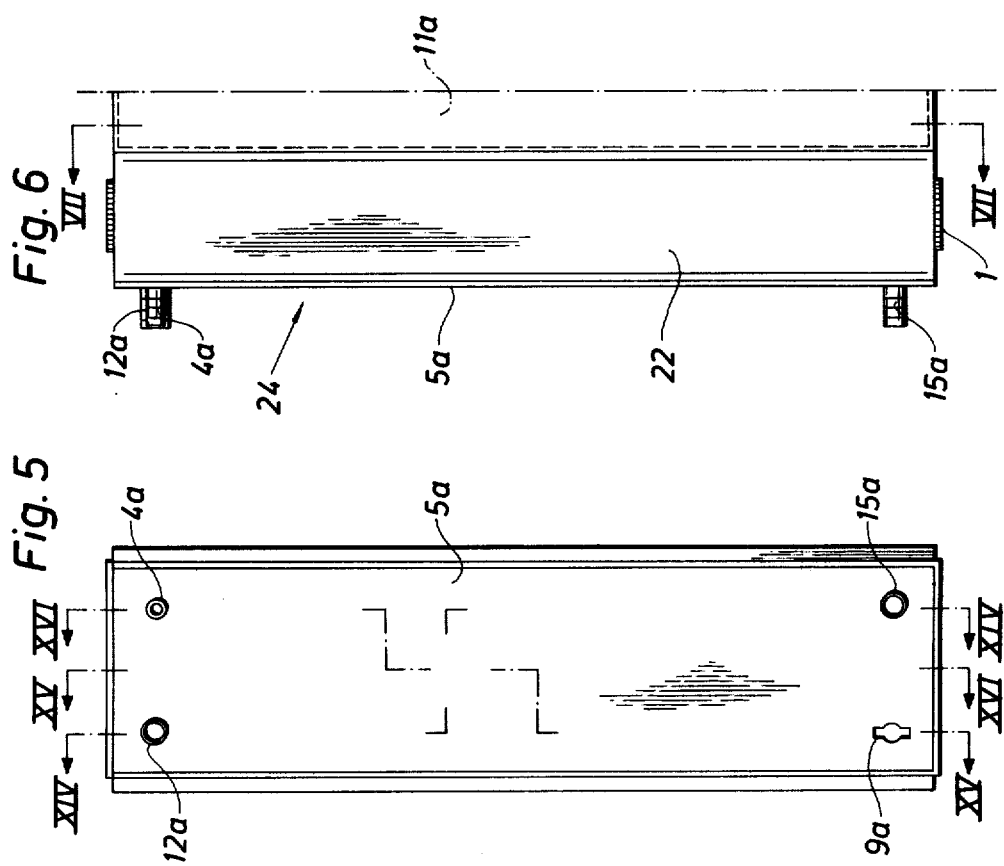

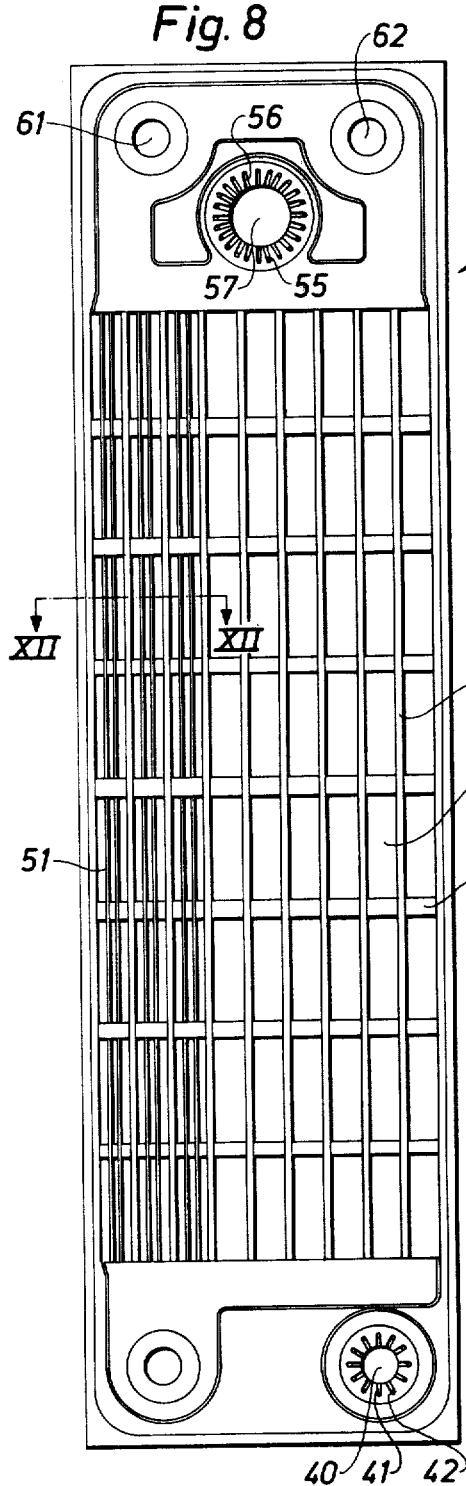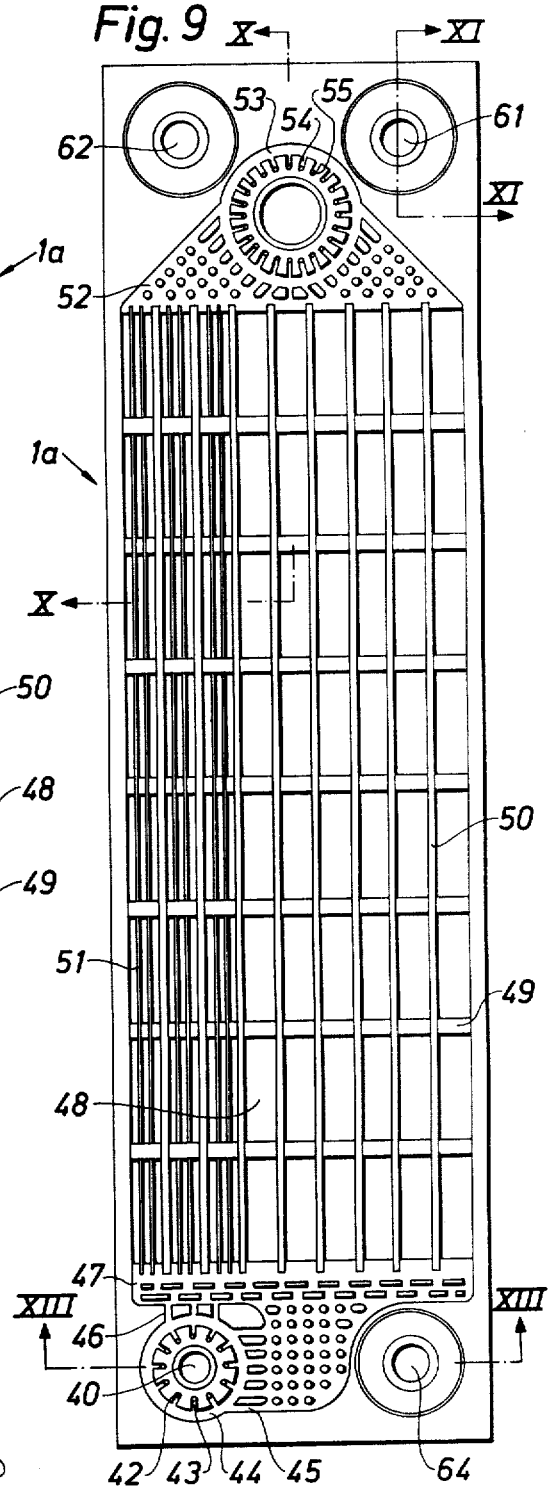

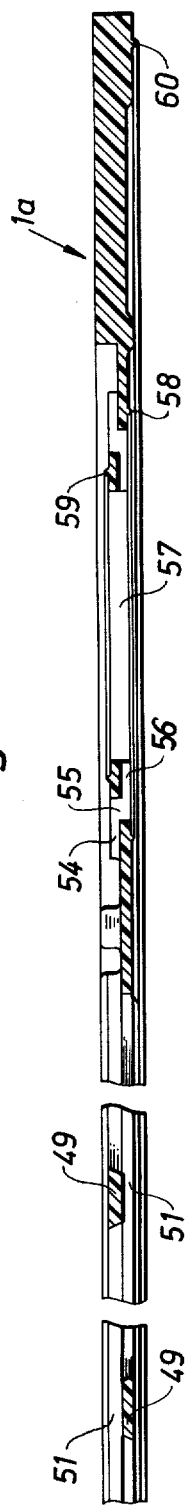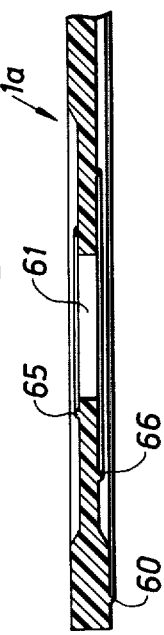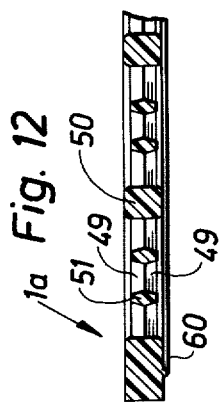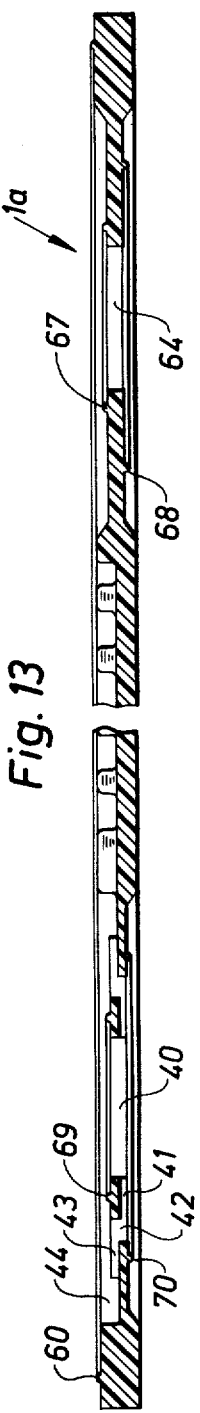

APPARATUS AND METHOD FOR THE DIFFUSION OF SUBSTANCES BETWEEN TWO FLUIDS SEPARATED BY A SEMIPERMEABLE MEMBRANE

BACKGROUND OF THE INVENTION

The present invention relates to an apparatus and method for the diffusion of substances between two fluids separated by a semipermeable membrane. More particularly, the apparatus of the present invention is mainly intended for use as blood oxygenator for mixing oxygen or oxygen containing gas into the blood of a patient before returning the blood to the patient.

Prior art blood oxygenators, which utilize a semipermeable membrane, such as for example, as shown in U.S. Pat. Nos. 3,212,498 and 3,332,746, have conducted a first fluid consisting of air, oxygen or some other oxygen mixture along one surface of a semipermeable membrane while the second fluid, consisting of blood to be oxygenated, is passed along the other opposing surface of the membrane. In this manner, a portion of the oxygen in the first fluid is diffused through the membrane and mixed with the blood flowing on the other side thereof.

In these prior art blood oxygenators however, only microscopic bubbles of oxygen or the gas mixture which are of a size capable of passing through the microscopic pores of the membrane are mixed with the blood, whereas larger bubbles of oxygen or gas mixture are excluded from passing through the membrane. In other words, with these prior art arrangements, the only means for oxygenating the blood is the diffusion through the microscopic pores of the membrane.

SUMMARY OF THE INVENTION

The present invention is directed to an improved apparatus and method for the diffusion of substances between two fluids separated by a semipermeable membrane and in the preferred embodiment, to an apparatus and method resulting in improved oxygenation of blood. In accordance with the present invention, the diffusion apparatus comprises at least one semipermeable membrane having first and second opposing surfaces, first conducting means for conducting a first fluid along the first surface of the membrane and second fluid conducting means for conducting the second fluid along the second surface of the membrane. The membrane is permable to at least a portion of the first fluid so that a portion of the first fluid is diffused through the membrane into the second fluid after the two fluids are conducted on the opposing sides of the semipermeable membrane. The diffusion apparatus further includes mixing means for directly mixing the first fluid into the second fluid after a portion of the first fluid has diffused into the second fluid.

The method of the present invention comprises passing a first fluid along one side of a semipermeable membrane which is permeable to a portion of the first fluid, passing a second fluid along the other side of the membrane whereby at least a part of the portion of the first fluid diffuses through the membrane and then directly mixing the first fluid into the second fluid after the part of the portion of the first fluid has diffused into the second fluid.

Such an apparatus and method, when employed as a blood oxygenator in which the first fluid comprises air, oxygen, or some other oxygen mixture and in which the second fluid consists of the blood to be oxygenated, achieves an improved oxygenation of the blood. This is a result of the fact that the present invention produces a fine distribution of microscopic bubbles of the gas mixture into the blood and then subsequently introduces the gas mixture directly into the blood in the form of large bubbles, thus improving the oxygenation of the blood. Further, the introduction of the large bubbles into the blood also facilitates the elimination of carbon dioxide from the blood.

In the preferred embodiment of the apparatus of the present invention, the mixing means comprises at least an aperture through the semipermeable membrane at the downstream side of the membrane. According to another preferred embodiment, the diffusion apparatus includes a pair of semipermeable membranes disposed with the first surfaces thereof opposing one another so that the first fluid conducting means conducts the first fluid between a pair of semipermeable membranes. In a still further preferred embodiment, the second fluid conducting means comprises a pair of spacing plates arranged in juxtaposition to the second surfaces of the pair of semipermeable membranes. These spacing plates include a plurality of flow channels for conducting the second fluid therein.

According to another preferred embodiment, the diffusion apparatus includes at least one tempering membrane having a first surface and a second surface, and third fluid conducting means for conducting a third fluid along the first surface of the tempering membrane and the second surface of the tempering membrane being in contact with the second fluid. Such a tempering membrane is thus useful in tempering of the second fluid.

According to a still other preferred embodiment of the present invention, elimination means are provided for eliminating a portion of the first fluid from the second fluid after the first and second fluids have been mixed with one another. In another preferred embodiment, the second fluid conducting means comprises a plurality of spacing plates arranged in parallel stacked relationship for conducting the second fluid therethrough and the apparatus further includes adjustable control means for controlling the introduction of the second fluid to only a predetermined number of spacing plates.

These and further features and characteristics of the present invention will be apparent from the following detailed description in which reference is made to the enclosed drawings which illustrate the preferred embodiment of the present invention.

BRIEF DESCRIPTION OF THE DRAWINGS

FIG. 2 shows relatively schematically a sectional view of the second preferred embodiment of the apparatus in accordance with the present invention;

FIG. 3 is an elevational view of the apparatus shown in FIG. 2 as viewed from the left-hand side;

FIG. 4 is a top cross-sectional view of the apparatus shown in FIG. 2;

FIG. 5 is an elevational view of the apparatus shown in FIG. 2 as viewed from the right-hand side;

FIG. 6 is an elevational view of the apparatus shown in FIG. 2 as seen in the direction against the plane of the drawing according to FIG. 2;

FIG. 7 is a cross-sectional view taken along lines VII—VII of FIG. 6;

FIGS. 8 and 9 show two elevational plan views of the opposite sides of a spacing plate useful in accordance with the apparatus of the present invention, a number of such spacing plates being used in the apparatus as shown in FIGS. 2-6;

FIG. 10 shows a sectional view taken along lines X—X of FIG. 9;

FIG. 11 shows a sectional view taken along lines XI—XI of FIG. 9;

FIG. 12 shows a sectional view taken along lines XII—XII of FIG. 8;

FIG. 13 shows a sectional view taken along lines XIII—XIII of FIG. 9;

DETAILED DESCRIPTION OF THE PREFERRED EMBODIMENT

The term fluid, in the foregoing as well as in the following, relates to gases as well as to liquids. Furthermore, as the apparatus and method in accordance with the present invention is intended mainly for use as a so-called blood oxygenator, the description for the present invention will be made with reference to such apparatus. However, it will be clear to those versed in the art that the apparatus and method can also be used in other cases where a successive mixing of a first fluid into a second fluid is desired, whether it is a matter of a gas into a liquid, a liquid into another liquid, or a gas into another gas.

Figure 1:
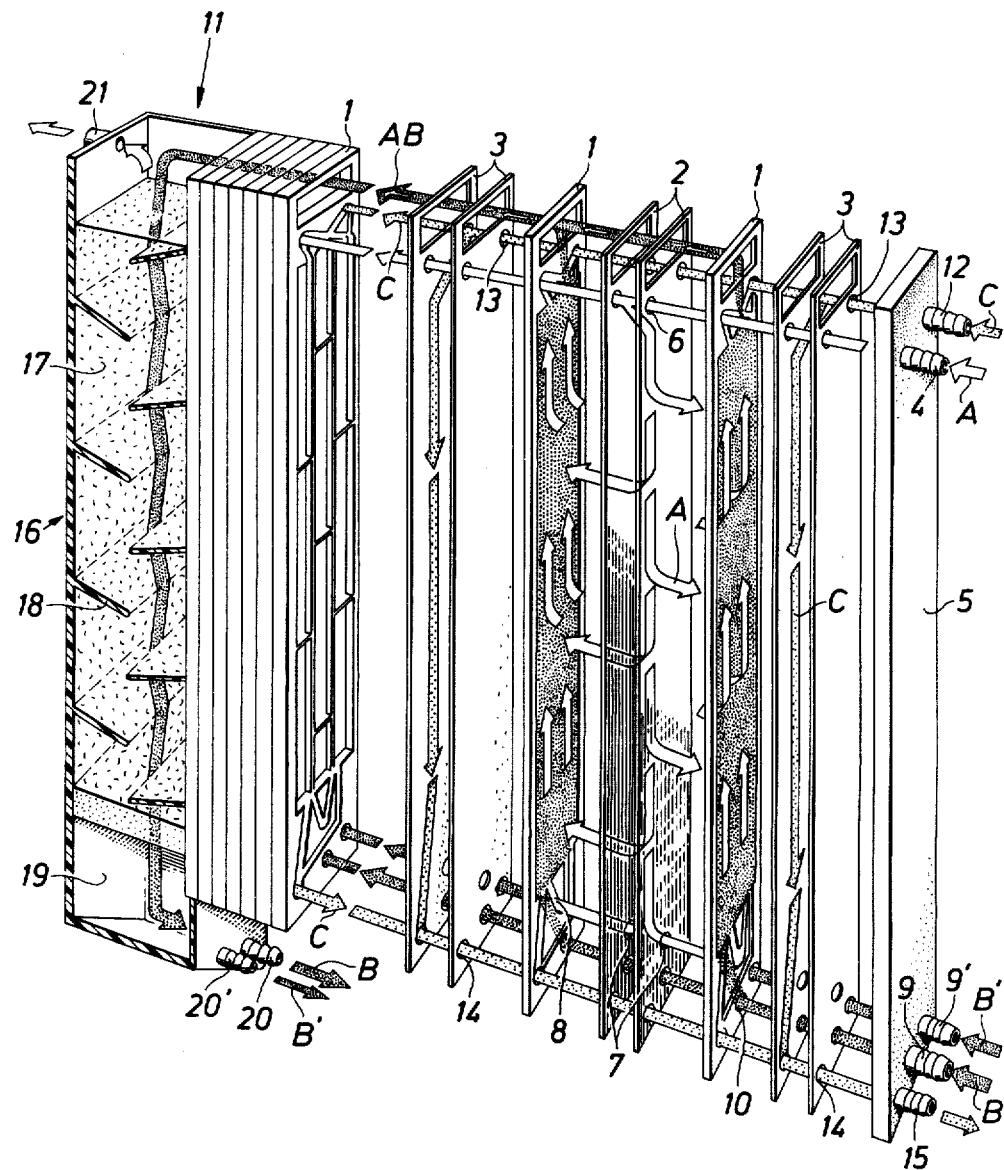
FIG. 1 shows relatively schematically an exploded view of a first embodiment of the apparatus in accordance with the present invention.

Referring now to FIG. 1, the apparatus in accordance with the present invention is comprised of a number of spacing disks or plates 1, provided with flow channels and with pairs of membranes 2,2 and 3,3 respectively, arranged between the spacing plates 1. The membranes 2 comprise semipermeable membranes which are adapted so as to allow a first fluid (i.e., a gas containing oxygen when the present invention is to be used as a oxygenator) to pass through the membrane in the form of microscopic bubbles. This first fluid may for example consist of air, oxygen, or some other oxygen mixture useful in oxygenating a second fluid, namely, blood.

The path of the gas is indicated in FIG. 1 by the arrows marked A. Accordingly, the gas is supplied through a connecting nozzle 4 in an end plate 5, and is conducted to a pair of membranes 2,2 to be subsequently introduced between them downwardly therethrough. For this purpose, the membranes 2 are provided at their upper ends with appropriate apertures 6 through which the gas is introduced between the membranes 2. At the lower ends of the membranes 2, apertures 7 are provided for conducting the gas out of the membranes 2. With the help of channels 8 provided in the spacing plates 1, the gas is conducted out of the membranes and is mixed directly into the second fluid, namely blood, being conducted on the opposite sides of the membranes 2.

The path of blood has been indicated in FIG. 1 by arrows marked B. Accordingly, the blood is introduced into the device through a connecting nozzle 9 provided in the end plate 5 and is conducted to apertures 10 provided in the lower ends of the spacing plates or disks 1. From these apertures 10, the blood is conducted further to the active part of the spacing discs or plates 1 via flow channels in the manner as described more fully in connection with the second embodiment of the subject invention described in the following. In the spacing plates 1, the blood is mixed with the gas which is diffused through the membranes and which is introduced through the channels 8. The blood is then discharged in the direction indicated by the arrow AB to the skimming section which is designated as a whole by the reference numeral 11. The arrow B' and the connecting nozzle 9' indicate an extra blood intake into the device which can be used in connection with special operations, such as for example coronary perfusion.

The arrow C shown in FIG. 1 indicates the path of a tempering fluid, for example water, which is supplied to and withdrawn from the device. This water is tempered either for cooling or for heating of the blood. As seen in FIG. 1, the water is introduced through a connecting nozzle 12 in the end plate 5. From there, the water is conducted by apertures 13 into the space between membranes, 3,3 which are preferably heat permeable. In the membranes 3,3 the water is conducted downwardly through the device and serves to temper the blood being conducted in the channels of the spacing plate 1 arranged along the opposite outer surfces of the membranes 3,3. The water is then withdrawn from the membrane in the device via apertures 14 and a connecting nozzle 15 in the end plate 5.

The skimming section 11 in the example shown consists of a substantially vertical shaft 16 which is filled with polyurethane foam 17 with open pores between inclined plates 18. At the bottom of the shaft 16 is connected a resevoir 19 with two outlets 20, 20' corresponding to the inlets 9, 9', respectively. Finally, numeral 21 designates an outlet for the skimmed off gas.

Thus, it is seen that in accordance with the apparatus and method of the present invention, the gas for oxygenation of the blood is first conducted along one surface of a semipermeable membrane 2 for diffusion of at least a portion of the gas through the membrane into the blood. At the downstream end of the membranes 2, the gas is then directly mixed into the blood (which is being conducted along the other side of the semipermeable membrane 2) through apertures 7 and channels 8. In blood oxygenation, such an apparatus and method first produces a very fine distribution of microscopic bubbles of the gas mixture into the blood. Then, subsequently, the gas mixture is directly introduced into the blood in the form of larger bubbles which do not pass by diffusion into the membrane. Owing to the microscopic bubbles diffused through the membrane 2, an effective oxygenation of the blood is achieved which is then further improved by the larger bubbles being introduced through the apertures 7. These larger bubbles in addition facilitates the elimination of carbon dioxide in the blood. In this regard, it should be noted that in order to avoid complete elimination of carbon dioxide, a small amount of carbon dioxide, for example 2-5%, is usually added to the gas mixture used, which otherwise consists substantially of oxygen gas.

It is further to be noted that this arrangement of the apparatus in which a first fluid (i.e., the gas) is conducted between pairs of membranes 2,2 arranged plane parallel to one another is similar to that used in connection with artificial kidneys of the plate type. It will be clear however to those versed in the arts that other basic constructions such as are used in artificial kidneys and dialyzers may also be used. For example, the membranes may be helically wound or may comprise tubular fibers as in other types of dialyzers.

In this regard, it should be further noted that as in dialyzers, the spacing elements or plates 1 in the form or disks having flow channels or the like are arranged in the apparatus between pairs of membranes 2,2 and 3,3. These spacing plates 1 are preferably adapted so that they conduct the second fluid, that is the blood, along the outside of the membranes in the pairs of membranes 2,2 and preferably in a counter flow in relation to the first fluid being conducted through the pairs of membranes 2,2. In this respect, the construction in accordance with the present invention thus differs from dialyzers which usually conduct the blood enclosed between two membranes or in tubes or fibers of membrane material.

Further, it is to be noted that although in the preferred embodiment, apertures 7 are provided for the direct mixing of the gas mixture into the blood after conduction of the gas mixture along the semipermeable membrane 2, such direct mixing may also take place in a different manner. For example, the gas mixture could be directly injected into blood channels before the blood is conducted to the membranes 2.

Still further, it is to be noted that the third fluid for tempering of the blood is appropriately separatd from the gas mixture by placing the tempering membranes 3,3 along the sides of the spacing element 1 remote from the semipermeable membranes 2,2,. This third fluid may either comprise a gas or a liquid which is intended for the heating or other tempering of the blood, and is preferably suitably arranged to conduct a third fluid in counter flow with respect to the blood.

The skimming section 11 has been provided for eliminating an excess of oxygen supplied and mixed into the blood before the blood is returned to the patient, which excess of oxygen is supplied in order to achieve an effective oxygenation of the blood.

Turning now to FIGS. 2-21, there is shown in greater detail a further embodiment of the apparatus in accordance with the present invention. For the parts corresponding to those of the construction illustrated in FIG. 1, the same reference designations have been used, but with the addition of an "a". As best seen in FIGS. 2-4, the construction of this further preferred embodiment comprises a number of spacing plates or disks 1a with pairs of membranes 2a and 3a respectively arranged between them. The spacing plate and membrane packet is held together by a clamping plate or end plate 5a which, with the help of clamping bars 22 is maintained pressed against a skimming unit 11a, the one end wall 23 of which has substantially the same shape as the clamping plate 5a. Blood is introduced via an inlet 9a which is shown in greater detail in FIGS. 20 and 21 described hereinbelow. In a similar manner, gas is introduced through an inlet 4a which is shown in greater detail in FIGS. 18 and 19, also discussed more fully hereinbelow.

The actual oxygenating and heating part of the device as a whole has been designated generally by numeral 24. The oxygenated blood leaves this section 24 via an outlet 25 and flows via a funnel 26 downwardly into a vertical shaft 27 which is formed by rings 28 and a base 29 of polyrethane foam or similar material with open pores therein. The skimmed off blood then drains into a collecting reservoir 30 and can be discharged via any of five different outlets 31, 32, 33, 34, and 35. The outlets 33, 34 and 35 are intended for connection to gauges for the measurement of pressure and temperature and for the taking of samples respectively. The actual main outlet for the blood to be returned to the patient is designated 32. Numeral 31 designates the special outlet which is intended for use in connection with, for example, coronary perfusion. Reference numeral 36 designates an outlet for skimmed off gas. This outlet 36 is preferably covered with a cap 37. Further, reference numerals 38 and 39 designate two inlets which may be utilized for the supply of different media, for example, heparin, etc.

As with the embodiment shown in FIG. 1, the main active portion of the apparatus 24 is comprised of a plurality of spacing plates or disks 1a provided with flow channels for conducting blood therein and with elongated membranes 2a, 3a, arranged in pairs for the gas mixture and for the heating medium, respectively, between the spacing plates 1a. Preferably, the membranes 2a for the gas mixture alternate with the membranes 3a for the heating medium between the spacing plates 1a.

The construction of the spacing plates 1a can best be seen in FIGS. 8-13. The blood inlet is designated in these figures generally by numeral 40. From this inlet 40, the blood flows first through channels designated 41 on one side of the plate 1a (see FIG. 8) to continue subsequently through the plate 1a via relatively small holes 42 and then further through ducts or channels 44, 45, 46, and 47 on the other side of the plate 1a (see FIG. 9) to the truly active portion or part of the plate 1a which is designated generally 48. This active part 48 of the plate 1a comprises transverse bars 49 which uphold longitudinal compression strips 50. Between the compression strips 50, the bars 49 uphold supporting strips 51 which alternatively face the two sides of the plate 1a, but which are somewhat retracted in relation to the outer surfaces of the compression strip 50. The oxygenated blood is subsequently removed via channels 52, 53, and 54 (see FIG. 9), through smaller holes 55 which extend through the plate 1a and further on the other side of the plate 1a (see FIG. 8) through channels 56 to an outlet opening 57.

Reference numerals 58, 59, and 60 designate different sealing beads which are shown most clearly in FIG. 10. These sealing beads 58, 59, and 60, with the help of special packings 75 (shown in more detail in FIG. 15) which press the adjacent membranes 2a, 3a against the sealing beads 58, 59 effectively seal the flow of blood from the other flow of gas and/or tempering fluid.

The gas and the tempering water are introduced via openings 61, 62 respectively and from there are further conducted between the membranes 2a, 2a or 3a, 3a with the help of special "buttons" which will be described in more detail hereinbelow in connection with FIGS. 14–16. The gas, after conduction along the surface of the membranes 2a, 2a is then introduced into the blood via apertures 63 in the membranes 2a, as most clearly shown in FIG. 17. These membranes 2a, 3a are provided moreover with further apertures 61', 62', 57', 40', and 64' corresponding to the holes 61, 62, 57, 40 and 64 respectively in the plate 1a. In this regard, it is appropriate here to compare FIG. 17 with FIG. 9. Reference numeral 64 designates the outlet for the water or the tempering fluid. Special buttons are also provided here, too, between the membranes, as more fully described in detail hereinbelow in connection with FIGS. 14–16.

Reference numerals 65 and 66 in FIG. 11, and 67 and 68 in FIG. 13, designate sealing beads which are intended to cooperate with the aforementioned buttons. In the same manner, the sealing beads 69 and 70 shown in FIG. 13 are intended to cooperate with the special packings 75.

FIG. 5 shows the apparatus in accordance with FIG. 2 as seen from the right. Numeral 4a designates the inlet for the gas mixture and 12a the water or tempering fluid intake. In the same manner, 9a designates the blood inlet and 15a the water discharge. For the rest, FIG. 5 illustrates essentially only the clamping plate 5a. In addition, however, the positions of the section lines XIV—XIV, XV—XV, and XVI—XVI are shown which correspond to the sections shown in more detail in FIGS. 14–16.

FIG. 6 illustrates the oxygenating section proper of the apparatus in accordance with the present invention, which as a whole is designated 24. This section is attached to the skimming section 11a with the help of clamping plates 5a and clamping bars 22.

FIG. 7 shows a section taken along lines VII—VII of FIG. 6. Numeral 25 designates the outlet for the oxygenated blood. The skimming section 11a is situated parly concealed behind its end wall 23 which has the same function as the clamping plate 5a—namely, tightly clamping together the plates 1a with the membranes 2a, 3a arranged therebetween.

Figure 14:
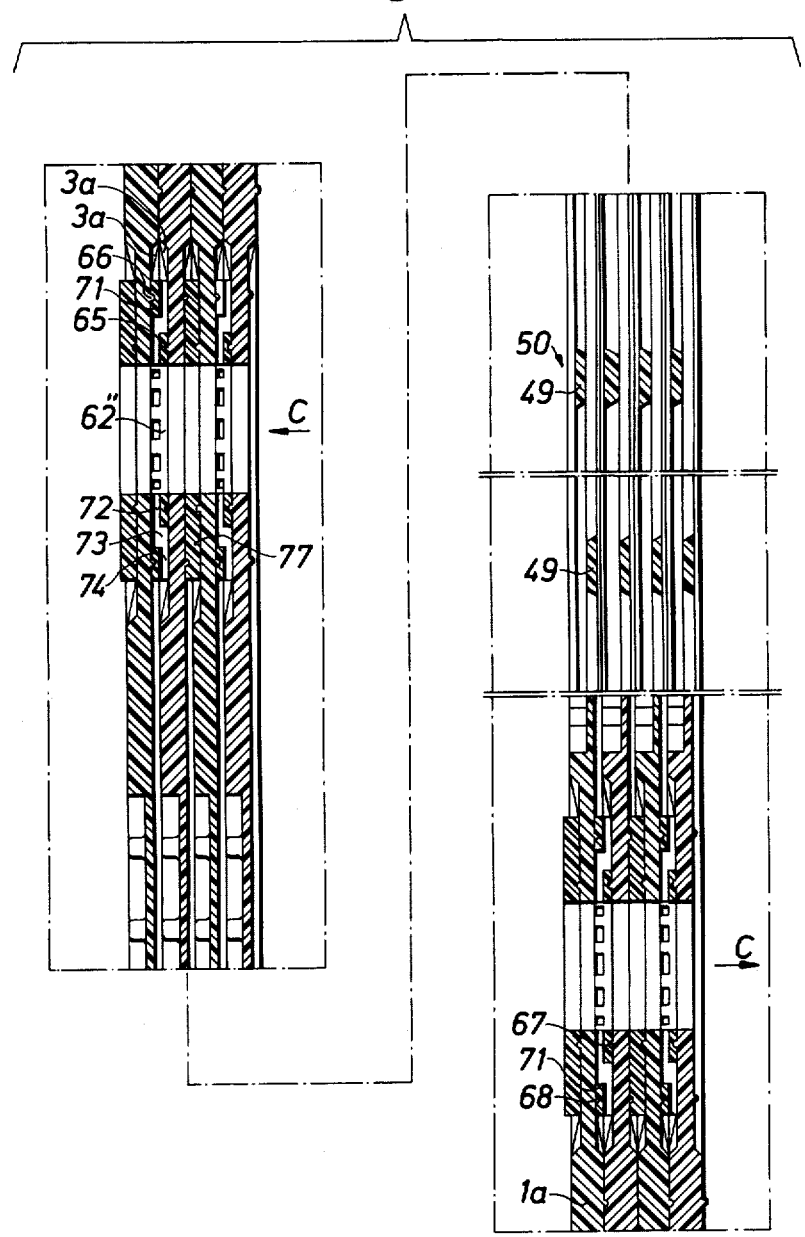
FIG. 14 shows a sectional view taken along lines XIV—XIV of FIG. 5.

FIG. 14 shows in greater detail how the water is introduced between the membranes 3a, 3a, how it is conducted therealong, and subsequently how it is removed from these membranes 3a, 3a with the help of special sealing buttons 71. These sealing buttons 71 which are placed between the membranes 3a, 3a each have a central opening 62'' from which the water is conducted through the channel 72 on one side of the button, through holes 73 extending through the buttons and then through channels 74 on the other side of the buttons 71. The buttons 71 are adapted so as to seal against the sealing beads which are identical with the sealing beads 65 and 66 shown in FIG. 11, but which surround the aperture 62. At the outlet end of the apparatus, similar and corresponding sealing buttons 71 are provided which press instead against the sealing beads 67, 68 on plate 1a as shown in FIG. 13, to form a seal so that the tempering fluid will be conducted through the outlet holes 64.

Figure 15:
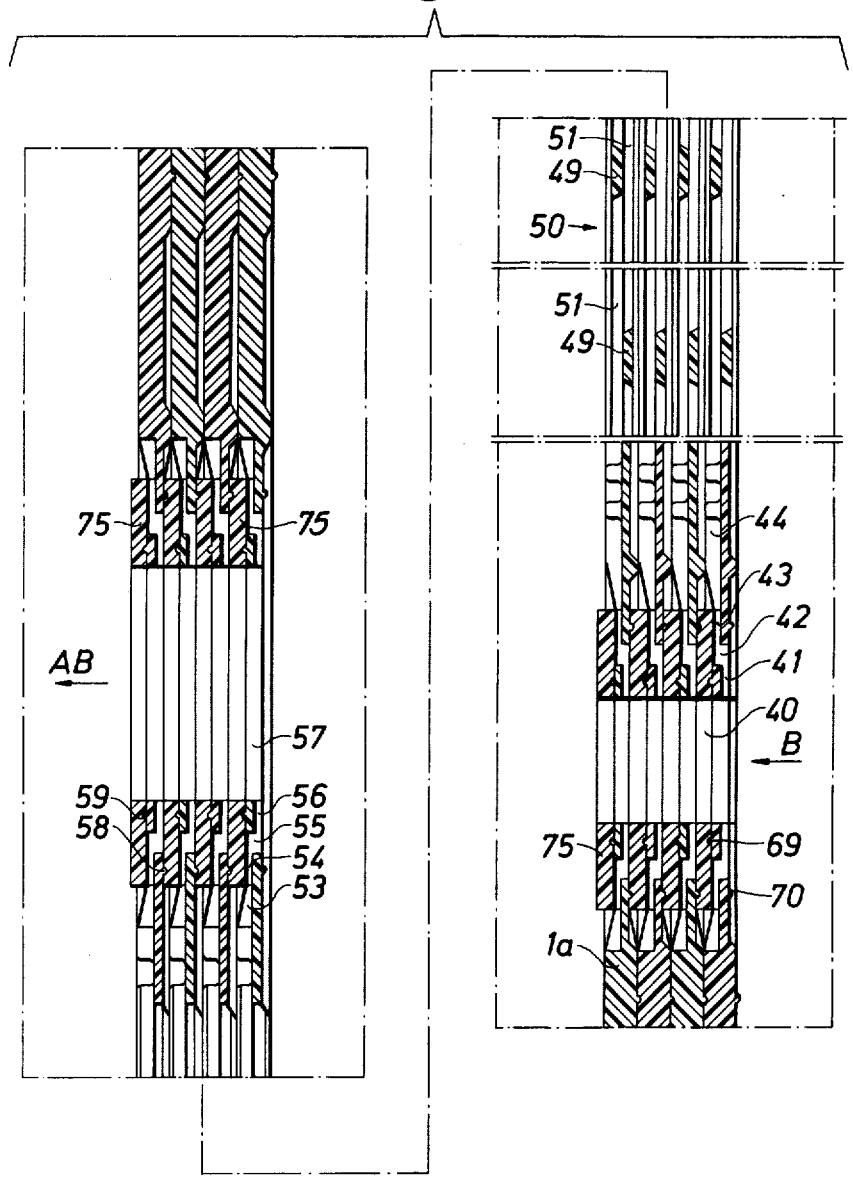
FIG. 15 shows a sectional view taken along lines XV—XV of FIG. 5.

In FIG. 15, there is shown how the blood is introduced at the place indicated by the arrow B and discharged in oxygenated state state at the place indicated by the arrow AB. The apertures and channels 40, 41, 42, 43, and 44 at the inlet end and the apertures and channels 53, 54, 55, 56, and 57 at the outlet end have previously been described with reference to FIGS. 8 and 9. With the help of sealing beads 69 and 70 at the inlet end, and 58 and 59 at the outlet end, the blood flow is effectively sealed off against the other flows of gas and water with the help of packings 75.

Figure 16:
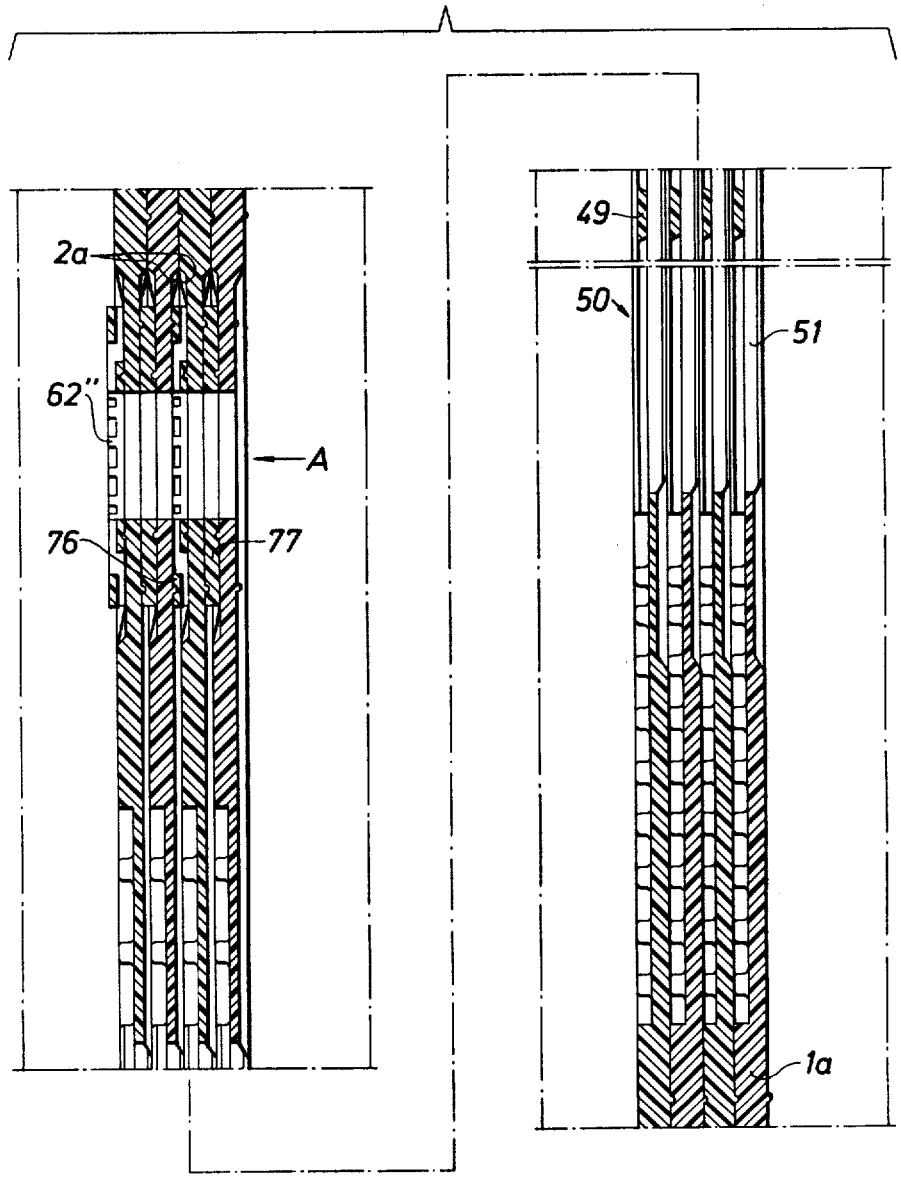
FIG. 16 shows a sectional view taken along lines XVI—XVI of FIG. 5.
Figure 17:
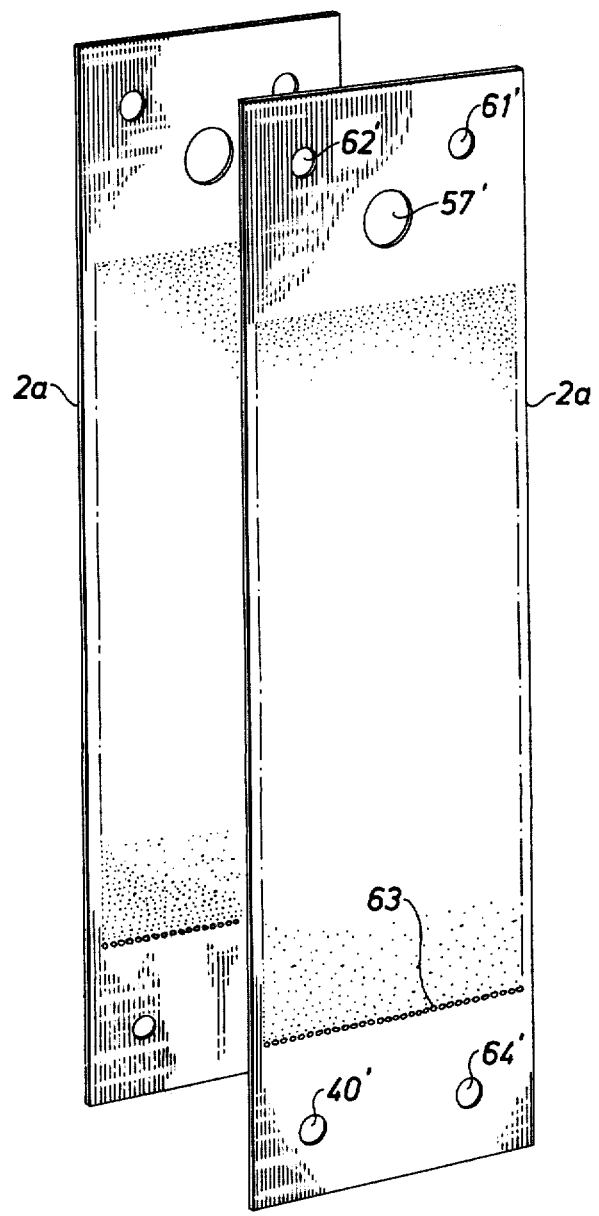
FIG. 17 shows a perspective view of two membranes, a number of which are intended to be arranged in pairs between the spacing plates of the type shown in FIGS. 8-13.

In FIG. 16, there is shown how the gas is introduced at the place indicated by the arrow A and is then conducted downwardly between the membranes 2a, 2a with the help of special sealing buttons 76. These sealing buttons 76 are substantially identical with the sealing buttons 71 described hereinabove with reference to the conduction of the tempering fluid and therefore need not be described in detail here. The gas mixture is conducted from the membranes 2a and into the blood flow partially by direct diffusion through the membrane 2a, and partially through a series of holes 63 provided at the lower ends of the membranes 2a, 2a, shown most clearly in FIG. 17. This series of small holes 63 preferably have a diameter of the order of magnitude of 50 microns which thus produces a high pressure drop and consequently an even distribution of the gas mixture.

With respect to the aforementioned diffusion of the gas mixture into the blood, it is preferable that the membranes 2a be microporous with pores or holes on the order of magnitude of 0.02 microns and of a thickness of approximately 20–25 microns. Examples of such membranes are various stretched PE or PP membranes, or expanded teflon membranes. Alternatively, various silicone membranes may be used which are not microporous in the true meaning of the word but wherein the diffusion takes place through the membrane material itself.

Reference numeral 77 designates "blind buttons" which are intended to be introduced into the membrane layers where a particular fluid is undesirable. In this manner, the gas mixture can be conducted through the pair of membranes 3a, 3a intended for the tempering water without being mixed with the tempering water or being conducted between the pair of membranes 3a, 3a. In a similar manner, the water or tempering fluid can be conducted through the pair of membranes 2a, 2a intended for the gas without being mixed with the gas or flowing into the space between the membranes 2a, 2a.

In FIGS. 14–16, there is shown again the transverse bars 49, the longitudinal compression strips 50, and the supporting strips 51. The truly active surface of the spacer plates 1a however has not been shown.

Figure 18:
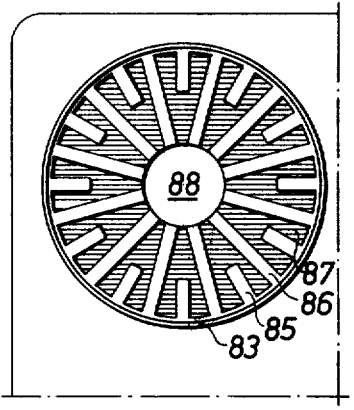
FIGS. 18 and 19 show on a larger scale a detail of the portion of the apparatus shown in FIG. 2 found within the circle designation XVIII-XIX.
Figure 19:
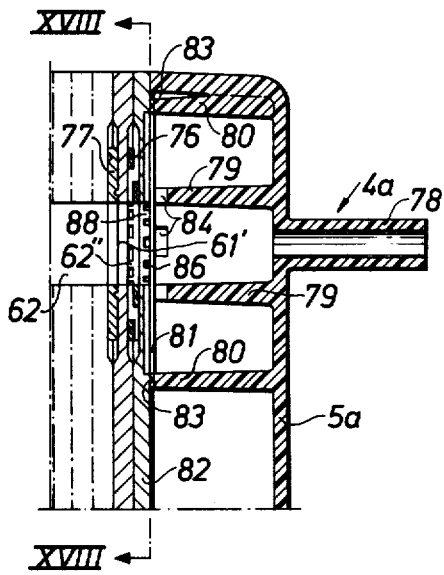

Referring now to FIGS. 18 and 19, which show on a larger scale the detail of FIG. 2 found within the circle designated XVIII-XIX, there is shown a gas inlet 4a for introduction of the gas mixture via a gas nozzle 78 which is preferably moulded onto the end plate or clamping plate 5a. With the aid of two inner concentric nozzles 79, 80, a filter 81 is pressed against an outer end plate 82. The sealing bead 83 provides an effective seal between the end plate 82 and the clamping plate 5a. With the help of channels 84, the gas mixture is guided over the entire surface of the filter 81. After filtration, the gas is conducted through the channel 62 formed by apertures 61' and 62''. Examples of usable filters are sintered PE or PP materials of a thickness of approximately 20 microns and a pore size of approximately 0.2–0.5 microns. Alternatively, a glass fiber material could be used.

FIG. 18 shows a section along lines XVIII—XVIII of FIG. 19 and thus shows the supporting surface proper for the filter 81. This supporting surface, which is thus located inside the sealing bead 83, is formed by radially arranged supporting strips 85 and 86 with channels in between which open out into a central opening 88.

Figure 20:
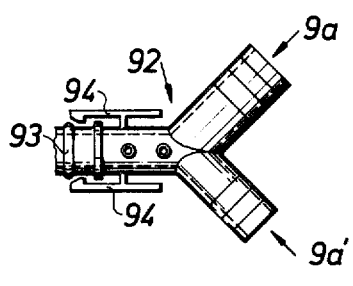
FIGS. 20 and 21 show on a larger scale a detail of the portion of the apparatus shown in FIG. 2 found within the circle designation XX-XXI.
Figure 21:
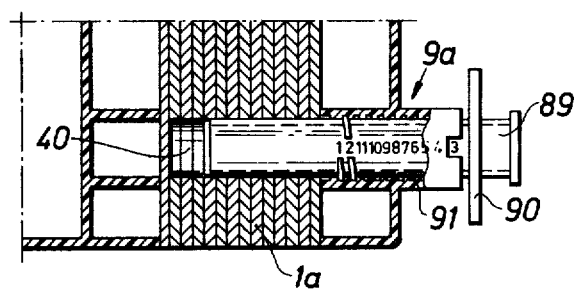

FIGS. 20 and 21 show schematically how the blood inlet 9a can be adapted for the setting of different capacities so that the same apparatus can be used for both adults as well as children. The inlet for the blood comprises a tubular plunger 89 which, with the help of a handwheel 90 and a thread 91, can be adjusted to different depths in the shaft or flow passage 40 formed by the apertures in the spacing plates 1a. The outer surface of the plunger 89 thus serves as a shut-off element for the flow channels 41 of those spacing disks 1a with which the plunger 89 is in blocking alignment. That is, the outer surface of the plunger 89 serves to close off to prevent the flow of blood to certain numbers of the spacing disks 1a, depending upon its depth into the shaft formed by the apertures 40 in the disks 1a. In the example shown, the device is set for treatment with three spacer disks 1a, and thus only the flow channels 41 of three of the spacer disks 1a are opened to receive blood introduced into the plunger 89. The remaining spacer disks are closed off by the outer surface of the plunger 89 to prevent the flow of blood therethrough. The capacity of the device can be increased fourfold in the embodiment shown by withdrawing the plunger 89 to its full extent to open the flow channels in all of the spacing disks 1a.

To the plunger 89, there is preferably connected a Y-coupling with two inlets 9a and 9a' corresponding to the inlets 9 and 9' in the construction according to FIG. 1. The seal between the Y-coupling 92 and the plunger 89 is achieved with the help of an O-ring 93 and the actual retention of the Y-coupling 92 is achieved with the help of hooks 94 which engage the enlarged end of the plunger 89.

While the preferred embodiment of the present invention has been shown and described, it will be understood that such is merely illustrative and that changes may be made without departing from the scope of the invention as claimed. Moreover, reference is made to U.S. Patent Application Ser. No. 6,250 filed on even date herewith, which presents substantial similarities of construction with that of the present application.

What is claimed is:

1. A diffusion apparatus for the diffusion of a gas into a liquid comprising:
   a pair of semi-permeable membranes each having first and second opposing surfaces and arranged with said first surfaces facing one another and said second surfaces facing away from one another, said semi-permeable membranes each being permeable to at least a portion of said gas;
   first introduction means for introducing said gas between said pair of semi-permeable membranes to be conducted along said first surfaces thereof;
   a pair of spacing plates arranged in juxtaposition to said second surfaces of said pair of semi-permeable membranes, said spacing plates including flow channels therein for conducting said liquid along said second surfaces of said semi-permeable membranes;
   second introduction means for introducing said liquid into said flow channels of said spacing plates to be conducted therethrough along said second surfaces of said semi-permeable membranes, whereby at least a first part of said portion of said gas diffuses through said semi-permeable membranes into said liquid to form bubbles of said diffused gas of a first size in said liquid; and
   mixing means associated with each of said semi-permeable membranes for directly mixing the second part of said gas into said liquid as said liquid is conducted through said flow channels along said second surfaces of said semi-permeable membranes so as to form bubbles of a second size larger than said first size in said liquid.

2. The diffusion apparatus of claim 1 wherein said mixing means comprises at least one aperture through each of said pair of semi-permeable membranes.

3. The diffusion apparatus of claim 2 wherein each of said pair of semi-permeable membranes is microporous with pores on the order of magnitude of 0.02 microns.

4. The diffusion apparatus of 3 wherein said mixing means further includes a series of apertures having a diameter on the order of magnitude of 50 microns through each of said semi-permeable membranes.

5. The diffusion apparatus of claim 1 wherein said semipermeable membranes have an inlet end and an outlet end and wherein said spacing plates have an inlet end and an outlet end, said inlet ends of said membranes being adjacent said outlet ends of said spacing plates and said inlet ends of said spacing plates being adjacent said outlet ends of said semipermeable membranes so that the direction of flow of said gas is counter to the direction of the flow of said liquid.

6. The diffusion apparatus of claim 1 including at least one tempering membrane for each of said spacing plates, each of said tempering membranes including a first surface and a second surface; and fluid conducting means for conducting a third fluid along said first surfaces of said tempering membranes; and wherein said second surfaces of said tempering membranes are in contact with said liquid being conducted through said flow channels of said spacing plates.

7. The diffusion apparatus of claim 6 including a pair of said tempering membranes for each of said spacing plates, said tempering membranes of each of said pairs of tempering membranes being disposed with said first surfaces opposing each other.

8. The diffusion apparatus of claim 7 wherein said tempering membrane is a heat permeable membrane for tempering said liquid.

9. The diffusion apparatus of claim 8 wherein said semipermeable membranes, said flow channels in said spacing plates and said tempering membranes each have an inlet end and an outlet end for the respective fluids being conducted therethrough, said inlet ends of said membranes being adjacent said outlet ends of said flow channels in said spacing plates, and said outlet ends of said membranes being adjacent said inlet ends of said flow channels so that said gas and third fluid are conducted in counterflow with respect to said liquid.

10. The diffusion apparatus of claim 9 further including a plurality of said pairs of semi-permeable membranes, a plurality of said pairs of tempering membranes and a plurality of said pairs of spacing plates, said plurality of spacing plates being arranged in a stack with one of said pairs of tempering membranes being disposed on one side of each of said spacing plates and one of said pairs of semi-permeable membranes being disposed on the other side of each of said spacing plates, and with each of said pairs of tempering membranes and each of said pairs of semi-permeable membranes being disposed between a pair of said spacing plates.

11. The diffusion apparatus of claim 10 wherein said stack of spacing plates with said pairs of membranes therebetween is adapted to be arranged vertically and wherein said membranes have inlet ends for said first and third fluids at the upper end of said stack and wherein said spacing plates have inlet ends for said second fluid at the lower end of said stack.

12. The diffusion apparatus of claim 10 wherein said mixing means comprises a series of apertures in at least one of said semi-permeable membranes of each of said pairs of semi-permeable membranes.

13. The diffusion apparatus of claim 1 further including elimination means for eliminating an excess portion of said gas from said liquid after said gas has been mixed with said liquid.

14. The diffusion apparatus of claim 13 wherein said elimination means comprises a skimming device adjacent the downstream end of said spacing plates for skimming off an excess of said gas in said liquid, and means for collecting said excess of said gas skimmed by said skimming device.

15. The diffusion apparatus of claim 14 wherein said skimming device comprises a porous substance through which said liquid is conducted to remove excess gas therein.

16. The diffusion apparatus of claim 15 wherein said porous substances is polyurethane.

17. The diffusion apparatus of claim 1 further including a plurality of said pairs of spacing plates for conducting said liquid therethrough, said spacing plates being connected in parallel in stacked arrangement; and adjustable control means for controlling the introduction of said liquid to only a predetermined number of said spacing plates.

18. The diffusion apparatus of claim 17 wherein said stacked spacing plates includes aligned inlet apertures defining a fluid passage through said stack for introduction of said liquid into said spacing plates and channels arranged in said spacing plates for conducting the liquid from said fluid passage through said spacing plates; and wherein said adjustable control means comprises a shut-off element movable to shut-off said channels of said spacing plates.

19. The diffusion apparatus of claim 18 wherein said shut-off element comprises a tubular plunger adjustably movable within said fluid passage, the outer surface of said plunger being adapted to block said channels in alignment therewith.

20. The diffusion apparatus of claim 1 wherein said gas comprises a gas containing oxygen and wherein said liquid comprises blood to be oxygenated, and wherein said semi-permeable membranes are permeable to a portion of the oxygen in said gas.

21. The diffusion apparatus of claim 20 wherein said semipermeable membranes are permeable to relatively small sized bubbles of oxygen and wherein said mixing means comprises apertures in said semipermeable membrane of a size to pass relatively large sized bubbles of oxygen in said gas.

* * * * *